United States Patent [19]

Langlois

[11] 3,983,529
[45] Sept. 28, 1976

[54] DETECTOR FOR USE IN ACOUSTIC HOLOGRAPHY
[75] Inventor: Gary Norris Langlois, Richland, Wash.
[73] Assignee: Holosonics, Inc., Richland, Wash.
[22] Filed: Mar. 28, 1975
[21] Appl. No.: 563,123

[52] U.S. Cl. .............................. 340/5 H; 73/67.5 H
[51] Int. Cl.² ..................... G01N 29/04; G01S 9/66
[58] Field of Search ................... 73/67.5 H, 67.5 R; 340/5 H, 5 MP

[56] References Cited
UNITED STATES PATENTS

| | | | |
|---|---|---|---|
| 2,155,659 | 4/1939 | Jeffree | 73/67.5 H UX |
| 3,493,073 | 2/1970 | Wolfe et al. | 73/67.5 H UX |
| 3,564,905 | 2/1971 | Brenden et al. | 73/67.5 H |
| 3,742,439 | 6/1973 | Sheridon | 73/67.5 H X |
| 3,832,888 | 9/1974 | Langlois | 73/67.5 H |

Primary Examiner—Richard C. Queisser
Assistant Examiner—John P. Beauchamp
Attorney, Agent, or Firm—Woodcock Washburn Kurtz & Mackiewicz

[57] ABSTRACT

An improved detector having a reflective surface which is substantially insensitive to vibration. The detection surface comprises a thin layer of liquid metal which is disposed over a substantially rigid, wettable substrate. In a presently preferred embodiment, the detector comprises a receptacle having disposed therein a rigid brass plate covered by a thin layer of mercury. The detector is submersed in a suitable fluid, such as water, to which an acidic substance has been added to reduce the pH of the fluid to the range of 5 to 6.

15 Claims, 4 Drawing Figures

DETECTOR FOR USE IN ACOUSTIC HOLOGRAPHY

BACKGROUND OF THE INVENTION

The present invention relates to the field of acoustical holography and, more particularly, to an improved liquid interface area detector for effecting acoustical imaging.

Acoustical holography, which involves the generation of holograms through the production of interfering patterns of acoustical waveforms, has been known for some time. One early example of an apparatus for practicing acoustical holography is disclosed in U.S. patent application Ser. No. 569,914 — Brenden, filed Aug. 3, 1966 and entitled "Ultrasonic Holography", now U.S. Pat. No. 3,879,989. In this patent means are shown for producing a pattern of perturbations at the interface of two fluids in response to the impingement of a pair of ultrasonic beams. The wave trains of each beam give rise to irregularities upon the liquid interface, the pattern of perturbations representing the phase relationships between various portions of the beams. By using one unmodulated beam as a reference, the pattern resulting from interference between it and a beam whose wavefront phase is spatially modulated will represent the characteristics of the modulation of the second beam.

Modulation of an acoustic beam may, for example, result from the presence of an object of varying acoustical transparency in the path of the beam. The interference pattern will then represent variations in the acoustical transmissivity of the object. In this manner a representation can be produced of the inner structure of an optically opaque object, such as flaws or voids within a metal casting or the arrangement of tissue within the human body.

In order to record or display the interference pattern given rise to by the reference and the object beams, it is known to illuminate the pattern with a beam of visible light. The light which is reflected from the pattern, hereinafter referred to as a hologram, is then directed to appropriate apparatus for recording or displaying the hologram.

While the science of acoustical holography has made substantial progress in recent years, many problems still exist in satisfactorily implementing the technique.

With one prior art approach, for example, a reference and an object beam are directed from beneath upon a detection device floating in an acoustically transmissive liquid. An illuminating beam of light is directed upon the top of the detector. In such an arrangement multiple reflections of acoustical energy within the detector structure degrade the quality of the hologram.

The detectors to be used with imaging systems have themselves presented substantial problems. In particular, many of the detectors heretofore known have been relatively inefficient, i.e., much of the acoustic and/or optical energy directed toward the detector was lost as a result of inefficient or unwanted reflection or due to absorption. In addition, most detectors, especially those utilizing a liquid-liquid interface, are particularly susceptible to extraneous vibrations. Such vibrations tend to cause spurious perturbations at the liquid interface, thus disturbing the pattern of the hologram and seriously affecting its quality. Further, most prior art liquid interface detectors required the passage of either the impingent light, the acoustic beams, or both through a window or membrane either before or immediately after encountering the hologram.

It is therefore an object of the present invention to provide an improved detector for acoustical holography apparatus.

It is another object of the present invention to provide a detector for use in acoustical holography which provides improved reflectivity to illuminating radiation.

It is still another object of the invention to provide a detector for use in acoustical holography which exhibits markedly improved stability against vibration.

SUMMARY OF THE INVENTION

Briefly stated, in accordance with one aspect of the invention the foregoing objects are achieved by providing a receptacle suitable for submersion in a sound transmissive fluid. A rigid substrate is disposed in the receptacle, and sufficient liquid metal added to cover the substrate. In a presently preferred embodiment the substrate comprises a thick brass plate, and the liquid metal is mercury. The receptacle is made of a material along whose surface the mercury will not migrate, and the transmissive liquid is water to which has been added sufficient hydrochloric acid to lower the pH of the solution to the range of 5 to 6. A reference and an imaging acoustic beam are directed through the water to the water-mercury interface to form a hologram at the surface of the mercury. A light source is directed obliquely upon the interface, the light reflected therefrom being directed to a suitable imaging apparatus.

BRIEF DESCRIPTION OF THE DRAWINGS

While the specification concludes with claims particularly pointing out distinctly claiming the subject matter which is regarded as the invention, it is believed that the invention will be better understood from the following description of a preferred embodiment taken in conjunction with the accompanying drawings in which:

DESCRIPTION OF A PREFERRED EMBODIMENT

Figure 1:
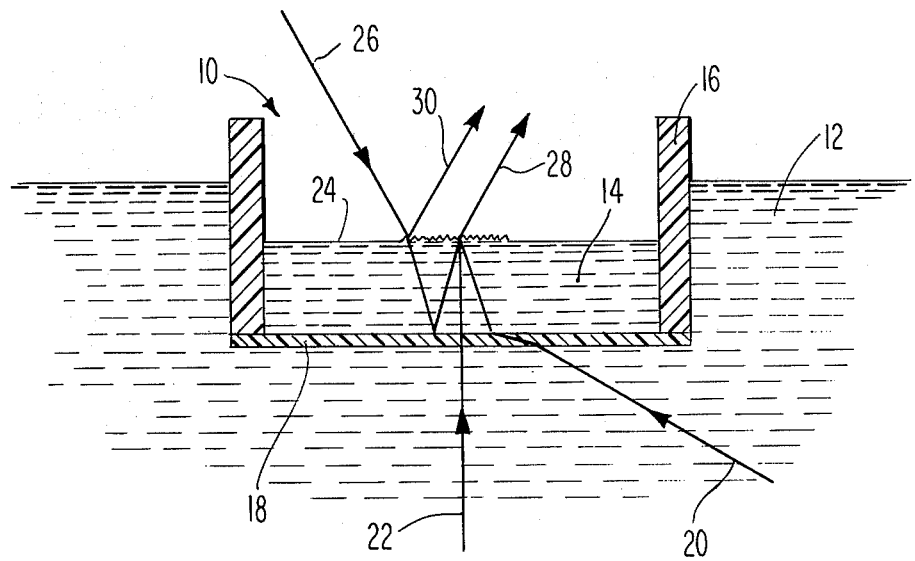
FIG. 1 illustrates one form of a prior art detector.

FIG. 1 represents one form of a detector presently used in acoustical holography. The detector, generally indicated at 10, is partially immersed in a liquid 12. Liquid 12 constitutes a medium through which acoustic signals may be transmitted with relatively low propagation losses; for many applications, water forms an economical and convenient medium. In the illustrated apparatus detector 10 is rigidly supported in liquid 12 by appropriate structure (not shown), and is partially filled with a detection liquid 14. The detection liquid is advantageously a material such as fluorinated ether which exhibits a relatively low surface tension so that sharply-defined perturbations may be readily formed thereon. The detection liquid 14 is retained within the detector by means of sidewalls 16, and by bottom membrane 18. In one operational scheme, membrane 18 comprises a thin film of black polyvinyl fluoride having a thickness in range of 0.13 mm. Such a material is advantageously provided with a low gloss or matte surface for reasons to be explained hereinafter.

Disposed within fluid 12 are two sources of acoustical energy (not shown) which may, for example, be electric-to-acoustic transducers. The first source produces a reference beam 20 which is directed against the membrane 18 which forms the lowermost surface of detector 10. At the same time the second source of acoustic energy directs a modulated or object beam 22 against membrane 18, impinging thereon at a substantially different angle than does reference beam 20. As is apparent from the Figure liquid 14 refracts the acoustic beams, substantially modifying the angle between them.

By placing an object to be examined in the path of object beam 22 the relative phase and magnitude of the advancing acoustic wavefronts are modified (spatially modulated), and in conjunction with the reference beam produce a unique interference pattern upon upper surface 24 of detector liquid 14. The interference pattern thus produced constitutes a hologram upon which is directed a beam of incident light 26. In order to minimize the reflection of the incident light from membrane 18, the membrane is typically provided with a low gloss or matte finish. Nonetheless, some of the incident light penetrates liquid 14. The light not absorbed by the liquid is reflected from bottom membrane 18 as indicated at 28. The balance of the incident light is reflected directly from the hologram formed at surface 24 of the detector. This reflected light, denominated 30 in the Figure, may then be viewed directly through the use of appropriate viewing optics, or received by suitable imaging apparatus such as a television or a photographic camera and used to produce a visible display which represents the object under inspection.

Figure 2:
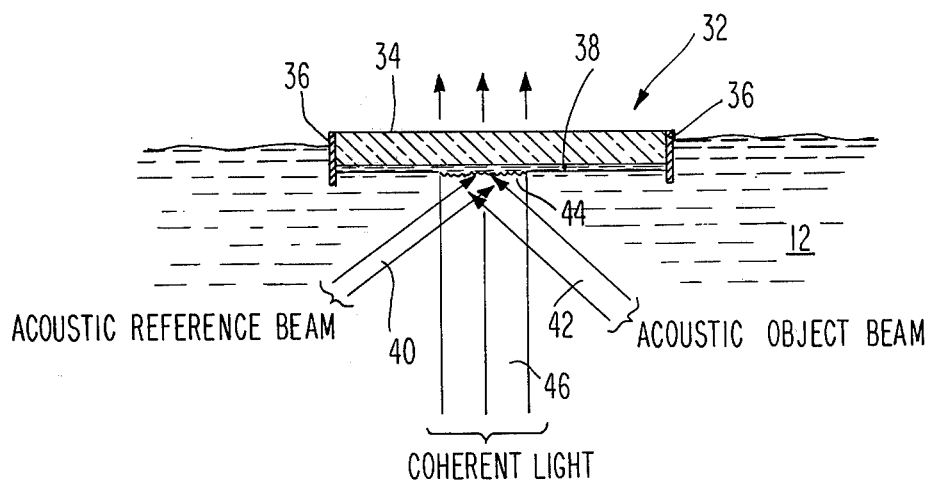
FIG. 2 represents another form of detection apparatus found in the prior art.

In FIG. 2 there is shown another form of detector 32 which is adapted to be at least partially submersed in a body of transmissive liquid 12. Such a detector, as set forth in U.S. Pat. No. 3,493,073 — Wolfe et al., includes an optically transparent plate 34 having a depending ridge 36 or similar means for encapturing a thin layer 38 of a pressure-sensitive detection fluid beneath the plate. Fluid 38 is of lesser density than transmissive fluid 12 and should be immiscible in liquid 12. The fluid must further be substantially optically transparent, as will be apparent from the ensuing description.

An acoustic reference beam 40 is directed upwardly through transmissive liquid 12 to an area upon the lower surface of pressure-sensitive detection fluid 38. At the same time an acoustic object beam 42, the phase of whose wavefronts are spatially modulated by the object to be examined, is also directed upon the same area of fluid 38 so as to give rise to a pattern of perturbations 44 at the surface of fluid 38 which represent the interference between wavefronts of the reference and object beams.

The pattern 44, or hologram, is illuminated from beneath by a beam of coherent light generally indicated at 46. The light must traverse the acoustically transmissive fluid 12, detection fluid 38 and plate 34 before emerging spatially modulated in accordance with the hologram 44 which has been formed at the surface of the detection fluid. The emergent light pattern may then be directly viewed, or may be recorded for subsequent display.

While both of the foregoing prior art hologram detection apparatus may be used to good effect, they nonetheless exhibit inherent disadvantages and give rise to substantial problems in making efficient use of acoustic and light energy. For instance, the pressure-sensitive fluids 14 and 38 which are used in the detectors of FIGS. 1 and 2 respectively are susceptible to disturbance by spurious outside vibrations. Further, the presence of membrane 18 in the embodiment of FIG. 1 necessarily attenuates both the reference and the object acoustic beams to some extent. Still further, the membrane acts to reflect not only the acoustic waves impingent thereon, but also a portion of the illuminating light which is directed upon the hologram formed at the upper surface of liquid. The detector of FIG. 2 requires the use of a substantially optically transparent detection fluid 38, which obviously places a strict limitation upon the range of materials which may be used. In addition to its attenuation by liquid 12 and fluid 38, the coherent light which is directed upon hologram 44 from beneath also necessarily undergoes further attenuation as it passes through plate 34.

Figure 3:
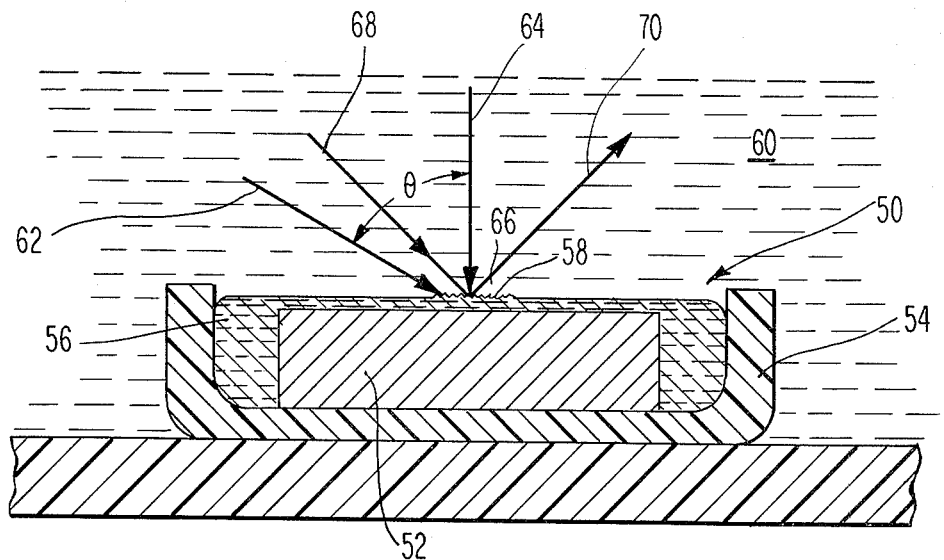
FIG. 3 is a cross-sectional diagram of a detector constructed in accordance with principles of the present invention.

Turning now to FIG. 3, there is shown an improved detector which forms the subject matter of the present invention and which obviates many of the problems experienced with prior art detection devices. The detector, generally indicated at 50, comprises a rigid substrate 52 which in a successfully tested embodiment was constituted by a brass plate having a thickness of approximately 2.5 cm. The substrate is disposed within an enclosure 54, and a liquid metal 56 added to the enclosure in sufficient quantity to form a thin layer over the upper surface of substrate 52.

In one successfully tested embodiment the layer of liquid metal overlying the brass substrate was adjusted to a depth of approximately 1 mm. While this dimension is not critical and may be varied to suit a given application, should the layer be unnecessarily thick it may become susceptible to disturbance by extraneous vibrations. On the other hand, if the layer is too thin it will not deform to the degree necessary to form a satisfactory hologram.

In a preferred embodiment, the liquid metal 56 is mercury. If mercury is used, it is important that enclosure 54 be of a material such as glass or plastic which does not exhibit an affinity for the mercury. By this is meant that the material of enclosure 54 is not one over whose surface the mercury will migrate.

In order to form an appropriate surface 58 for the production of a holographic image, it is highly desirable that the upper surface of substrate 52 be flat and smooth. In practice it has been found that good results are achieved by maintaining the surface of the substrate flat within a tolerance of ⅛ of the shortest acoustic wavelength to be utilized. Further, in order to support a relatively thin layer of liquid metal the substrate surface must be of a material which will be wetted by the liquid metal. When the liquid metal used is mercury, a brass surface has been found to provide the requisite wetting characteristic. Further, by using a brass substrate an additional benefit accrues in that the brass-mercury interface exhibits a low reflection coefficient for acoustic energy so that most of the acoustic energy which penetrates the layer of mercury is absorbed by the brass substrate.

To prevent spurious vibrations from arising in the substrate, it is advisable that it be securely fastened to a rigid foundation, or that it be of substantial mass. A further advantage accruing in the use of a substrate of appreciable thickness is the absorption of impingent acoustical energy. In one successfully tested embodiment a brass substrate having a thickness of approximately 2.5 cm was used to good effect.

In use, detector 50 is immersed in a body of transmissive fluid 60 which may, for instance, be water. In actual use, it has been found that the interface between mercury 56 and water becomes somewhat cloudy, particularly when the pH of the water is 7 or greater. Although the mercury still exhibits a substantially higher degree of reflectivity than an interface between air and fluorinated ether, as in FIG. 1, the reflectivity of the mercury surface can be still further improved by maintaining the pH of the transmissive fluid in the range of approximately 5 to 6. This can easily be achieved by adding an appropriate amount of hydrochloric acid to the water. With a bright surface on the mercury it reflects approximately 75% of incident visible light, as compared with approximately 1.4% for the fluorinated ether-air interface.

In order to create the perturbations in the surface 58 of the liquid metal which constitutes a hologram, a pair of acoustic beams 62 and 64 are directed thereon. In the illustrated embodiment, beam 64 represents an acoustic object beam, the phase of whose wavefronts have been modulated as the result of their passage through an object to be examined. Beam 62 represents a reference acoustic beam which is of the same frequency as beam 64. In a preferred mode of construction the object beam 64 is oriented normal to the surface 58 of liquid metal 56, while reference beam 62 is inclined at a relatively large angle $\theta$ with respect to beam 64. In one successfully tested embodiment, an angle $\theta$ of approximately 60° to 75° was found satisfactory.

In order to optically reproduce the hologram 66 which is given rise to by interfering wavefronts of the acoustic beams, or to form an optical image using the hologram, a light beam 68 is directed obliquely upon surface 58. The beam is then diffracted and refracted from the hologram 66. The resulting light 70 can then be used to form an optical image of the hologram, or of the object, which may be displayed upon a screen or recorded by suitable means for display at a subsequent time.

While in a presently preferred embodiment a brass substrate is utilized in conjunction with mercury, it will be recognized by those skilled in the art that other materials may alternatively be selected. For example, another example of a liquid metal-substrate combination which lends itself to use in the detector shown in FIG. 3 is liquefied gallium distributed over a glass substrate. It is known that gallium wets a glass surface and that liquid gallium provides a reflective surface. Further, gallium is not susceptible to evaporation and/or diffusion losses and may therefore be used in air. On the other hand, it is thought that a layer of gallium may be less sensitive to impingent acoustic signals than will mercury.

It will, of course, be seen that other liquefied metals such as cesium or rubidium may be selected for use, and that many materials other than the examples recited herein are well suited for use as substrates. In addition, the use of enclosure 54 is exemplary only, it being apparent that means for constraining liquid metal 56 might be formed integrally with the bottom of the enclosure which contains transmissive liquid 60; or the substrate could be placed directly over the floor of the enclosure, and the upstanding sidewalls of the enclosure used to confine the liquid metal. Still other variations of the inventive detector disclosed herein may additionally be thought of, it being recognized that the particular construction disclosed herein represents only the best mode currently known to the inventor.

Figure 4:
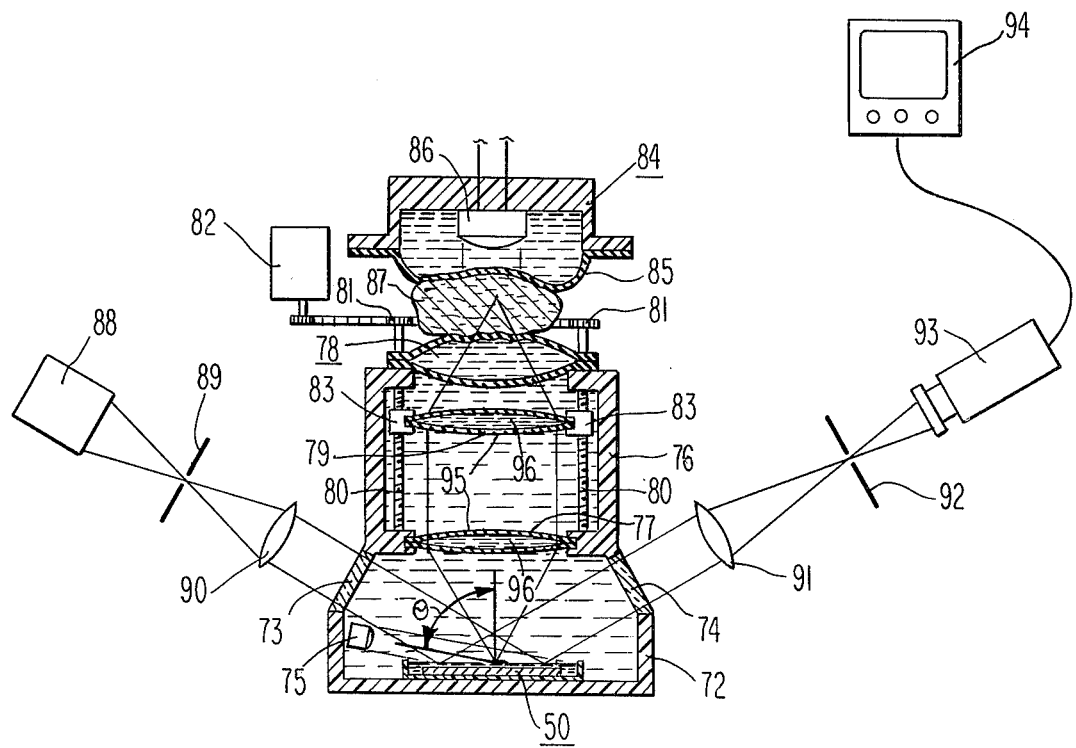
FIG. 4 is a cross-sectional view of an improved imaging system incorporating the detector of FIG. 3, and constructed in accordance with the teachings of the present invention.

FIG. 4 shows an acoustical imaging system, and depicts one implementation of the detector which was illustrated at FIG. 3. The imaging system forms the subject matter of copending U.S. application Ser. No. 563,219 filed Mar. 28, 1975, now U.S. Pat. No. 3,964,052. The detector 50 is disposed at the bottom of a first, lower enclosure 72. In the lateral walls of enclosure 72, and at approximately opposite sides thereof, are disposed a pair of optically transmissive windows 73 and 74. An acoustic transducer 75, which may for instance be of piezoelectric type, is mounted within enclosure 72 and directed at an oblique angle to the liquid metal surface of detector 50.

A second enclosure 76 is disposed above the first enclosure 72, and is separated therefrom by a partition in which is inserted an acoustic lens 77. The upper end of enclosure 76 is sealed by means of a liquid-filled closure 78. Closure 78 advantageously comprises an envelope made of natural rubber or the like which is filled with a quantity of water. Natural rubber is a preferred material for the closure as, among the commonly available materials, it is the least absorptive of acoustic energy. In addition, natural rubber produces only minimal reflection of an impingent acoustic signal.

Disposed within the upper enclosure 76 is a second acoustic lens 79 which cooperates with lens 77 to focus an acoustic object beam upon detector 50. Various types of acoustic lenses are known, for instance, as shown in U.S. Pat. No. 3,765,403 — Brenden. In a preferred embodiment, an envelope 95 of polystyrene may be used for the outer surfaces of the lenses 77 and 79. The envelope 95 is filled with a liquid 96 which may advantageously be Freon 113, "Freon" being a trademark used by the E. I. du Pont de Nemours Corporation to designate a particular type of fluorinated hydrocarbon.

Also disposed within second enclosure 76 are a plurality of lead screws 80 which extend vertically through the enclosure, the upper ends of the screws being linked by means of sprockets 81 to a chain so that they may be rotated in synchronism by means of suitable driving means such as electric motor 82. Followers 83, which may comprise recirculating ball nuts, are threadedly engaged by the lead screws and are affixed to a frame carrying movable lens 79. In this manner lens 79 may be moved to an appropriate vertical position in order to focus the acoustic object beam upon the surface of detector 50.

Disposed above the water-filled closure 78 is still another enclosure generally designated 84, one wall of which comprises a flexible membrane 85 and which is filled with a suitable sound-transmissive liquid such as water. Also disposed within enclosure 84 is a transducer 86 which produces a beam of acoustic energy. The latter beam, referred to as the object beam, is directed through membrane 85 to an object 87 to be inspected. It will be recognized by those skilled in the art that the use of flexible membranes for contacting the object to be inspected allows the transmissive fluid to be brought into close proximity with the object, so that any discontinuities in the path of an impingent acoustic beam will be those within the object. In other words, it is desirable that spatial modulation of the object beam occurs only in response to characteristics of the object under inspection, and not because of any discontinuities, voids, or other variations in the media through which the beam passes.

The upper surface of detector 50 is illuminated by electromagnetic energy from source 88. While the energy will be referred to as "light" and treated as visible light for purposes of description, it is readily apparent to those skilled in the art that infrared and ultraviolet light, as well as monochromatic light, may be used. In addition other forms of electromagnetic radiation outside the visible portion of the spectrum may be selected for a particular adaptation of the present invention.

In the embodiment shown, an opaque element 89 having a small aperture or "pinhole" therein is utilized in conjunction with source 88 to provide an effective point source of light. In this manner, light is produced which is at least partially coherent. It may alternatively be desired to use totally coherent light, in which case a laser may be provided. One such device which is believed to be particularly adaptable for use with the disclosed invention is a laser of the pulsed Argon ion type.

The light produced by the source is directed upon a suitable lens 90 and passes through window 73 to impinge upon the surface of detector 50 at an oblique angle.

Acoustic transducer 75 is also directed toward the surface of the detector. In a preferred embodiment, the angle θ formed between the object beam and the reference beam is in the range of approximately 60° to 75°. The inventor has found that as the angle θ increases, increasing amounts of energy can be supplied by the reference beam. This is important since a higher-energy reference beam produces commensurately better resolution at the detector surface, and in particular can be used to achieve good resolution in the presence of an object beam of very low energy. In this manner, a lack of energy in the object beam may be compensated for by an increase in energy of the reference beam, assuming that the angle θ between the object and reference beams is sufficiently large. By using a sufficiently large angle θ and a sufficiently energetic reference beam, the amount of acoustic energy necessary to properly ensonify the object 87 under inspection can be minimized. By reducing the amount of energy required for ensonifying the object, the likelihood of injury to living tissue is reduced and the utility of the system in examining living organisms is enhanced.

Light reflected from the surface of detector 50, and representing the hologram formed thereon by the interfering acoustic beams escapes from lower enclosure 72 through window 74 and is collimated by means of lens 91. It is likely that the light reflected from the surface of detector 50 will contain a number of diffracted beams, as explained in U.S. Pat. Nos. 3,564,904 and 3,564,905 — Brenden et al. and U.S. Pat. Nos. 3,585,847 and 3,765,403 — Brenden. The diffracted beams are focused at different points by lens 91. A spatial filter which, for instance, may comprise a thin plate 92 having a pinhole aperture about 400 microns in diameter, selectively transmits the desired component of the reflected light to appropriate means for recording and/or displaying the hologram. In the illustrated embodiment, a video camera 93 is shown coupled to a television receiver 94 so that the hologram produced at the surface of detector 50 may be viewed immediately upon production.

In operation, transducers 75 and 86 are energized so that acoustic energy from transducer 86 ensonifies object 87. The varying density of object 87 spatially modulates the phase of the object beam, which is transmitted through closure 78 and into the upper enclosure 76. Motor 82 is then operated to raise or lower lens 79 to an appropriate position to focus, in conjunction with the second lens 77, the acoustic energy penetrating object 87 upon the surface of detector 50. At the same time, a reference beam of acoustic energy from transducer 75 is caused to impinge upon the surface of the detector at an angle θ with respect to the object beam.

In a preferred embodiment, transducers 86 and 75 are excited by means of radio frequency signals to produce wave trains at a frequency in the range of 0.5 to 15 MHz. It has been found advantageous to pulse or repeat wave trains in the indicated frequency range at a frequency below approximately 1 kHz, the wave trains of each pulse persisting for a period of approximately 100 microseconds. Of course, it is desirable that the wave trains produced by transducers 86 and 75 be of the same frequency so as to produce a meaningful interference pattern upon the surface of the detector of the system.

Due to the disposition of detector 50 at the bottom surface of the first enclosure 72, it is relatively immune from vibration when compared to the immersed detectors found in the prior art. Moreover, it will be seen that by providing two separate enclosures the integrity of the lower enclosure can be maintained despite the introduction of dirt, impurities, etc. into the upper enclosure. The latter problem is particularly acute when an operating mechanism, such as the lens positioning apparatus shown in FIG. 4, is present within the upper enclosure.

It will be appreciated by those skilled in the art that if impurities are introduced into the transmissive fluid in the lower chamber they may attack or react with the liquid metal used in the detector. For this reason it is especially important to maintain the purity of the fluid in the lower chamber. Still further, it may be found desirable to use different fluids in the first and second chambers. For instance, should mercury be used as the liquid metal in detector 50, it will be desirable to use an aqueous hydrochloric acid solution in the lower enclosure which has a pH in the range of from 5 to 6. The solution, however, may have a detrimental effect upon the mechanism in the upper enclosure, or may alternatively necessitate the use of materials which are expensive and/or difficult to work with in the fabrication of the mechanism. Aside from this, there may be still other reasons necessitating the use of two different fluids in the first and the second enclosures. In any of these cases, the use of separate but juxtaposed fluid enclosures is a highly desirable attribute of the illustrated apparatus.

Another advantage of the illustrated acoustic imaging system is the fact that it makes it unnecessary to place a detector above an object to be ensonified. In addition, with the vertical orientation of the object beam transducer, the object to be ensonified, the various lenses, and the detector, it is unnecessary to provide the system with complex and expensive reflecting elements to orient the acoustic and/or electromagnetic beams in a useful configuration.

As will be evident from the foregoing description, certain aspects of the invention are not limited to the particular details of the examples illustrated, and it is therefore contemplated that other modifications or applications will occur to those skilled in the art. It is accordingly intended that the appended claims shall cover all such modifications and applications as do not depart from the true spirit and scope of the invention.

What is new and desired to be secured by Letters Patent of the United States is:

1. Improved detector apparatus responsive to impingent acoustic wavefronts to form a hologram, comprising:
   a rigid substrate having a continuous substantially planar upper surface;
   a layer of liquid metal covering said planar upper surface;
   said upper surface of said substrate being formed of a material which is wetted by said liquid metal;
   said layer of liquid metal being thinner than the thinnest layer of said metal which could exist upon a planar surface of a material not wetted by said metal; and defining an upper surface and defining a lower surface in intimate contact with the upper surface of said rigid substrate;
   a mass of a second liquid, said layer of liquid metal being submersed in said second liquid;
   first transducer means positioned to direct a beam of object-modified acoustic energy through said second liquid directly onto the upper surface of said layer of liquified metal;
   second transducer means positioned to direct a reference beam of acoustic energy through said second liquid directly onto the upper surface of said layer of liquid metal;
   the beam from said second transducer means being oriented at a predetermined angle with respect to the beam from said first transducer means to give rise to a pattern of disturbances on said upper surface of said layer of liquid metal; and
   means for directing illuminating energy upon the pattern of disturbances.

2. A detector as defined in claim 1, further including liquid retaining means disposed about said substrate for confining said liquid metal thereon.

3. A detector as defined in claim 2, wherein said liquid metal is mercury.

4. A detector as defined in claim 3, wherein said second liquid is water.

5. A detector as defined in claim 4, wherein said second liquid has a pH in the range of approximately 5 to 6.

6. A detector as defined in claim 5, wherein said second liquid comprises water and hydrochloric acid, said second liquid having a pH from approximately 5 to approximately 6.

7. A detector as defined in claim 6, wherein said substrate is composed of brass.

8. A detector for use in an acoustic imaging system including means for directing an object-modulated acoustic beam thereon, means for directing a reference acoustic beam thereon, and means for illuminating the area of the detector impinged upon by said acoustic beams, comprising:
   a substrate disposed beneath said means for directing and having a substantially planar upper surface;
   a layer of liquified metal disposed upon said planar surface and having a lower surface in intimate contact with said substrate and an upper surface oriented in the path of the acoustic beams;
   means for retaining said liquified metal upon said planar surface;
   said substrate being formed of a material which substantially absorbs acoustic energy which traverses said layer of liquified metal and impinges upon said substrate.

9. A detector as defined in claim 8, wherein said liquified metal is mercury.

10. A detector as defined in claim 9, wherein said mercury forms a layer over said planar surface having a thickness of approximately 1 mm.

11. A detector as defined in claim 10, wherein said substrate is rigid.

12. A detector as defined in claim 11, wherein said planar surface is composed of brass.

13. A detector as defined in claim 11, wherein said substrate is formed of a material which is wettable by said liquified metal.

14. An ultrasonic holography imaging method comprising the steps of:
   a. providing a substantially rigid substrate, which is wettable by a liquified metal;
   b. disposing a layer of said liquified metal over said substrate to form a readily deformable upper surface, said layer being thinner than the thinnest layer which could exist upon a substrate not wettable by said liquified metal;
   c. submerging said layer of liquified metal in a second liquid;
   d. directing a first, object-modified beam of acoustic energy through said second liquid directly upon said upper surface;
   e. directing a second, reference beam of acoustic energy through said second liquid directly upon said upper surface, said second beam lying at a predetermined angle to said first beam to produce a disturbance pattern upon said upper surface; and
   f. illuminating said disturbance pattern.

15. An ultrasonic holography imaging method comprising the steps of:
   a. providing a liquid-retaining enclosure;
   b. providing a substantially continuous planar substrate within said enclosure;
   c. disposing a layer of liquified metal over said substrate, said liquified metal wetting said substrate so as to form a thin layer thereon, said layer being thinner than the thinnest layer which could exist upon a non-wettable substrate;
   d. submersing said layer of liquified metal in a second, acoustically-transmissive liquid;
   e. directing a first, object-modified and a second, reference beam of acoustic energy through said second liquid directly upon the upper surface of said liquified metal to produce a disturbance pattern thereon; and
   f. directing a beam of electromagnetic radiation upon the disturbance pattern to illuminate said pattern.

* * * * *